United States Patent [19]

Osterholm

[11] Patent Number: 4,963,130

[45] Date of Patent: Oct. 16, 1990

[54] INTRA-PERITONEAL PERFUSION OF OXYGENATED FLUOROCARBON

[75] Inventor: Jewell L. Osterholm, Radnor, Pa.

[73] Assignee: Thomas Jefferson University, Philadelphia, Pa.

[21] Appl. No.: 932,459

[22] Filed: Nov. 18, 1986

Related U.S. Application Data

[63] Continuation of Ser. No. 757,015, Jul. 19, 1985, Pat. No. 4,657,532.

[51] Int. Cl.$^5$ ............................................. A61M 21/00
[52] U.S. Cl. ......................................... 604/24; 604/28; 604/51; 604/26; 519/10
[58] Field of Search ..................... 604/23–29, 604/51, 52; 514/10; 118/632; 501/791

[56] References Cited

U.S. PATENT DOCUMENTS

| | | | |
|---|---|---|---|
| 4,105,798 | 8/1978 | Moore et al. | 514/755 |
| 4,378,797 | 4/1983 | Osterholm | 604/27 |
| 4,393,863 | 7/1983 | Osterholm | 604/52 |
| 4,402,984 | 9/1983 | Moore | 514/755 |
| 4,443,480 | 4/1984 | Clark, Jr. | 514/755 |
| 4,445,500 | 5/1984 | Osterholm | 604/52 |
| 4,445,514 | 5/1984 | Osterholm | 128/632 |
| 4,445,887 | 5/1984 | Osterholm | 604/51 |
| 4,445,888 | 5/1984 | Osterholm | 604/28 |
| 4,445,892 | 5/1984 | Mussein et al. | 604/101 |
| 4,446,154 | 5/1984 | Osterholm | 514/10 |
| 4,446,155 | 5/1984 | Osterholm | 514/10 |
| 4,450,841 | 5/1984 | Osterholm | 128/632 |
| 4,451,251 | 5/1984 | Osterholm | 604/27 |
| 4,464,169 | 8/1984 | Semm | 604/26 |
| 4,495,886 | 5/1984 | Osterholm | 604/51 |
| 4,661,092 | 4/1987 | Popovich et al. | 604/26 |

OTHER PUBLICATIONS

Krone et al., "Long Term Perfusion of the Isolated Rat Liver Maintenance of its Functional State by iv of Fluorocarbon Emulsion" in *Biochemica et Biophysica Acta* 372 (1974), 55–71.

Faithfull et al., "Whole Body Oxygenation Using Intraperitoneal Perfusion of Fluorocarbons" in B. J. Anaesth. (1984), 56, pp. 867–872.1

A. V. Beran and W. F. Taylor, "Peritoneal Dialysis for the Support of Respiratory Insufficiency in Rabbits," Journal Science, 43, 695–703 (1972).

P. Collipp, "Peritoneal Dialysis for the Respiratory Distress Syndrome," *JAMA*, Jan. 15, 1968, vol. 203, No. 3, p. 169.

J. A. Awad, A. Brassard, and W. M. Caron, "Intraperitoneal Oxygenation, An Experimental Study in Dogs," *International Surgery*, vol. 53, No. 3, pp. 162–166 (Mar. 19).

Creager, *Human Anatomy and Physiology*, Wadsworth, Inc., 1983, p. 541.

J. A. Awad, A. Brassard, W. M. Caron and C. Cadrin, "Intraperitoneal Oxygenation with Hydrogen Peroxide," *International Surgery*, vol. 54, No. 4, pp. 276–282 (Oct. 1970).

Renvall, et al., "Kinetics of Oxygen in Peritoneal Cavity," *J. of Surgical Research* 28, 132–139 (1980).

Renvall et al., "Intraperitoneal Oxygen and Carbon Dioxide Tensions in Experimental Adhesion Disease and Peritonitis," *The Amer. J. of Surgery*, vol. 130, pp. 286–292 (Sep. 1975).

*Primary Examiner*—C. Fred Rosenbaum
*Assistant Examiner*—Mark O. Polutta
*Attorney, Agent, or Firm*—Woodcock Washburn Kurtz Mackiewicz & Norris

[57] ABSTRACT

A novel method of oxygenating the tissue of a living mammal is disclosed comprising the steps of providing an oxygenated fluorocarbon-containing liquid; injecting that oxygenated liquid into the peritoneal cavity of said mammal; and withdrawing said fluorocarbon liquid from said cavity, said injecting and withdrawing be conducted at a rate sufficient to oxygenate said tissue. Accordingly, a novel "artificial lung" is disclosed which is useful to selectively oxygenate the body of a mammal, as reflected by increased arterial blood gas (pO$_2$) in said mammal.

2 Claims, No Drawings

INTRA-PERITONEAL PERFUSION OF OXYGENATED FLUOROCARBON

This application is a continuation of U.S. Ser. No. 757,015, filed July 19, 1985, and issued as U.S. Pat. No. 4,657,532, on Apr. 14, 1987.

FIELD OF THE INVENTION

This invention relates generally to artificial respiratory devices and methods, and more particularly to chemical methods for providing whole body oxygenation of a mammal whose respiratory system is partially or completely inoperative. More particularly, the present invention relates to methods and devices for treating mammals suffering from anoxia.

CROSS-REFERENCE TO RELATED APPLICATIONS AND PATENTS

This application is related to U.S. Ser. No. 428,900, filed Sept. 30, 1982, abandoned entitled "Stroke Treatment Utilizing Extravascular Circulation Of Oxygenated Synthetic Nutrients To Treat Tissue Hypoxic And Ischemic Disorders" (TJU-3-12), and is also related to U.S. Ser. No. 582,961, filed Feb. 23, 1984 of the same title (TJU-3-13) now U.S. Pat. No. 4,686,085. U.S. Ser. No. 582,961 (TJU-3-13) is, in turn, a division of U.S. Ser. No. 428,850 filed Sept. 30, 1982, now U.S. Pat. No. 4,445,500 (TJU-3-11), which along with U.S. Ser. No. 428,900 (TJU-3-12) are both, in turn, divisions of U.S. Ser. No. 354,346, now U.S. Pat. No. 4,445,886 (TJU-3-3) and which, in turn, is a continuation-in-part of U.S. Ser. No. 139,886 (now U.S. Pat. No. 4,378,797 (TJU-3), all of which are incorporated herein by reference as if set forth in full.

The present application is also related to the following issued United States patents, all of which are incorporated herein by reference as if set forth in full, and all of which are divisions of one or more of the other of the aforementioned U.S. Ser. Nos. 139,886 (TJU-3) and 354,346 (TJU-3-3): U.S. Pat. No. 4,445,514 (TJU-3-1); U.S. Pat. No. 4,393,863 (TJU-3-2); U.S. Pat. No. 4,450,841 (TJU-3-4); U.S. Pat. No. 4,445,887 (TJU-3-5); U.S. Pat. No. 4,446,154 (TJU-3-7); U.S. Pat. No. 4,446,155 (TJU-3-8); U.S. Pat. No. 4,451,251 (TJU-3-9); U.S. Pat. No. 4,445,888 (TJU-3-10); U.S. Pat. No. 4,445,500 (TJU-3-11).

BACKGROUND OF THE INVENTION

There are many post-traumatic and post-operative patients who develop major pulmonary complications which interfere with or preclude adequate oxygenation. The "shock lung" best characterizes this syndrome complex. Severe pneumonias, smoke inhalation, acute respiratory obstructions, pre-mature birth, and birth-related pulmonary injury also can lead to the same general problems with oxygenation. Patients with massive pulmonary embolism and hemothorax also suffer from severe hypoxemia. Combining patients in these categories, there is a substantial population of patients at high risk, but whose conditions are potentially reversible, given adequate oxygenation.

The present invention utilizes an oxygenated fluorocarbon liquid for general body oxygenation, which is applied as a circulation through the peritoneal cavity. The aforementioned incorporated patents and patent applications reference in detail various prior art publications relating to fluorocarbons and their medical uses.

More recently, in the *British Journal of Anaesthesia* 56:867 (1984) in an article entitled "Whole Body Oxygenation Using Intra Peritoneal Perfusion of Fluorocarbons" by Faithfull, Klein, van der Zee and Salt, results of a preliminary study undertaken to assess the feasibility of increasing the arterial oxygen tension, and decreasing the arterial carbon dioxide tension, in intact animals, by means of peritoneal perfusion with the perfluorocarbon-containing, oxygen-transporting blood substitute, 20% Fluosol-DA, were disclosed. This *British Journal of Anaesthesia* article is not believed to be prior art to the present application.

See also U.S. Pat. No. 4,402,984 (Moore).

SUMMARY OF THE INVENTION

The present invention provides a novel method of whole body oxygenation of the tissue of a living mammal comprising the steps of: providing an oxygenated fluorocarbon-containing liquid; injecting said oxygenated fluorocarbon liquid into the peritoneal cavity of said mammal; and withdrawing said fluorocarbon liquid from said cavity, said injecting and withdrawing being conducted at a rate sufficient to oxygenate at least a portion of the tissue of said mammal. In accordance with the preferred embodiment of the present invention, an oxygenated fluorocarbon emulsion having an aqueous component, a fluorocarbon component, and an emulsification component is utilized which is oxygenated to a $pO_2$ in excess of 500 mmHg prior to injection. The preferred rate of injection is above 20 milliliters per minute per kilogram of body weight of said mammal, preferably about 25 milliliters per minute per kilogram of said body weight. In the preferred embodiment, the perfusion rate is selected to increase the arterial blood gas of said mammal. Accordingly, the method of the present invention provides a novel "artificial lung" which may be used to provided sufficient oxygen to the blood to maintain life even in the presence of complete or near complete respiratory failure.

These and other objects of the invention will become apparent from the following more detailed description.

DESCRIPTION OF THE PREFERRED EMBODIMENTS

The present invention provides a novel method for oxygenating the tissue of a living mammal employing an oxygenated fluorocarbon containing liquid. The preferred fluorocarbon containing liquid is the oxygenated fluorocarbon nutrient emulsion which is disclosed in my aforementioned United States patents, such as U.S. Pat. No. 4,445,886, which has been incorporated by reference as if fully set forth herein. Although this fluorocarbon containing emulsion is presently preferred, it is anticipated that certain constituents presently contained in this emulsion may be eliminated from the fluorocarbon containing liquid used in accordance with the preferred embodiment of the present invention. For example, to minimize the likelihood of bacterial growth, glucose may be eliminated from the fluorocarbon emulsion formulation. Similarly, the subject amino acids and steroids in the subject composition may be eliminated, if desired. Although not presently preferred, it is within the scope of the present invention to inject a liquid consisting essentially of the oxygenated fluorocarbon itself. In this treatment modality, it will be preferred to follow this fluorocarbon treatment with a lavage intended to wash remaining fluorocarbon from the peritoneum at the conclusion of treatment. This lavage may comprise injecting isotonic saline with or without a detergent or emulsifier, such as the pluronic disclosed in the aforementioned patent, to thereby reduce the likelihood of long term toxicity. Under most circumstances, it will be preferred that either or both of the subject perfusate and the subsequent lavage contain an antibiotic, such as bacitracin, to minimize the incidence of peritoneal infection.

In order to ensure that substantial oxygen transfer will occur, it is presently preferred to oxygenate the subject fluorocarbon containing liquid to a $pO_2$ in excess of 500 mmHg prior to injection. As reported in the aforementioned patents, these oxygen tensions are easily obtainable with the subject oxygenated fluorocarbon emulsion.

The present invention was reduced to practice, and its utility demonstrated, through performance of the following examples:

Experiments were begun using a male 11 pound orange tabby cat which was anesthetized using a 35 milligram per kilogram intra-muscular injection of ketamine. Thirty minutes later, 20 milligrams of flexedil, a respiratory paralytic was administered at 20 milligrams intravenously, and the animal then placed on a respirator. After 20 minutes, its arterial blood was determined to have a pH of 7.430, a $pCO_2$ of 25.5, and a $pO_2$ of 103. The aforementioned oxygenated nutrient emulsion (using the fluorocarbon FC-80) was placed in a Harvey pediatric oxygenator (volume 1230 cc) and maintained at about 40° C. Large (½ to ¾ inch) cannulas were placed through two flank incisions into the peritoneum. A Randoff pump was initially used to inject the oxygenated fluorocarbon nutrient emulsion into the peritoneum through one of the cannulas, the second cannula being routed back to the oxygenator for recirculation and reoxygenation of the subject fluorocarbon emulsion. After 10 minutes of administration of a 90% $N_2O$-10% $O_2$ respiratory gas mixture, the pH of the arterial blood was determined to be 7.374, the $pCO_2$ to be 28.2, and the $pO_2$ to be 48. Perfusion of the peritoneal space was established at a flow rate greater than 200 milliliters per minute. Problems were encountered, however, with the patency of the return line. Apparently, fatty tissue was being drawn into the return line, a condition which persisted until the catheters were manipulated into the space below momentum, which resolved the problem. Before the collection of meaningful data could be obtained, however, an inadvertent disconnection of the respirator resulted in the expiration of the test animal. Accordingly, a second series of tests were performed using a male, white and grey, 9½ pound cat. At 2:05 p.m. 150 milligrams of ketamine and 0.18 milligrams of atropine were administered intra-muscularly. At 2:15 p.m. a 70/30 mixture of $N_2O/O_2$ was begun through a respirator. At 2:30 p.m. 20 milligrams of flexedil was administered. The arterial blood gas at 2:35 p.m. registered a $pCO_2$ of 43.2, a $pO_2$ 313; the pH was 7.283. The relatively higher small $pO_2$ of this arterial blood gas is considered within the normal range given the possibility of some hyperventilation and the administration of a respiratory gas containing 30% oxygen. At 2:35 p.m. the respirator was adjusted to increase the volume to 45 from 35. At 2:50 p.m. the arterial blood gas was 36 $pCO_2$, 306 $pO_2$, at a pH of 7.318. At 2:55 p.m. a 90/10 N mixture was substituted as the respiration gas. At 3:05 p.m. the aforementioned fluorocarbon emulsion from the Harvey pediatric oxygenator was determined to have an oxygen tension of 565, a carbon dioxide tension of 25, and a pH of 7.951. At 3:10 p.m. the arterial blood gas of the subject animal had an oxygen tension of 48, a carbon dioxide tension of 33.4 and a pH of 7.335. At 3:15 p.m. the arterial blood gas of that animal exhibited a $pO_2$ tension of 28 mmHg, a carbon dioxide tension of 38.4 mmHg and a pH of 7.354. At 3:24 p.m. the carbon dioxide tension was 43.5, the oxygen tension 36 and the pH 7.311. At 3:36 p.m. the carbon dioxide tension was 37.8, the oxygen tension 36, and the pH 7.292. At 3:58 p.m. the pH was 7.260, the carbon dioxide tension was 42.4, and the oxygen tension was 34. At 4:05 p.m. the oxygen tension of the injected and withdrawn fluorocarbons was determined. The fluorocarbon injected was determined to have an oxygen tension of 594 and a pH of 6.815; the fluorocarbon withdrawn from the peritoneum was found to have a $pO_2$ of 511 and a pH of 6.865. The carbon dioxide tension in the withdrawn fluid was determined to be 26.7, but was not determined for the input fluorocarbon at this time. At 4:15 p.m. the arterial blood gas was determined to have a pH of 7.212, a carbon dioxide tension of 40.7 and a $pO_2$ of 42. At 4:20 p.m. the fluorocarbon was determined to have pH of 7.612. Unfortunately, the $pO_2$ electrode used to determine oxygen tensions in this test was apparently poisoned by the fluorocarbon, and therefore provided doubtful accuracy. It is believed that it was recalibrated, and at 4:20 p.m. the arterial blood gas pH was found to be 7.170, the $pO_2$ tension to be 46, and the carbon dioxide tension to be 36.3. Return flow, i.e., withdrawal of the fluorocarbon containing liquid from the peritoneum, was improved in this test by routing the exit cannula to a ballast receptacle at atmospheric pressure which was then used as an intermediate reservoir to supply the oxygenator input. As seen from the above, a systemic arterial $pO_2$ of approximately 30 mmHg (i.e., 28-36 mmHg) was achieved by drastic hypoventilation. When oxygenated fluorocarbon was perfused through the cat peritoneum at rates of about 200 to 250 milliliters per minutes, this severe hypoxia was alleviated, as indicated by increased systemic $pO_2$ of about 46 mmHg.

Accordingly, the method of the present invention has been demonstrated as being useful in treating systemic anoxia under conditions where the subject mammal's respiratory system is not capable of providing normal arterial $pO_2$ tensions.

I claim:

1. A method of oxygenating the tissue of a living mammal, comprising the steps of:
   (a) providing an oxygenated fluorocarbon containing liquid;
   (b) injecting said oxygenated fluorocarbon liquid into the peritoneal cavity of said mammal;
   (c) withdrawing said liquid from said cavity;
   said injecting and withdrawing being conducted at a rate sufficient to oxygenate at least a portion of the tissue of said mammal, wherein said oxygenated fluorocarbon liquid comprises an oxygenated fluorocarbon containing aqueous emulsion.

2. The method of claim 1 wherein said oxygenated fluorocarbon containing aqueous emulsion comprises an aqueous component, a fluorocarbon component and an emulsification component.

* * * * *